United States Patent

Garner et al.

[11] 4,115,450
[45] Sep. 19, 1978

[54] BIS-AMINOARYLETHANE AMIDE COMPOUNDS

[75] Inventors: Robert Garner, Bury, England; Jean Claude Petitpierre, Kaiseraugst, Switzerland

[73] Assignee: Ciba-Geigy Corporation, Ardsley, N.Y.

[21] Appl. No.: 773,988

[22] Filed: Mar. 3, 1977

Related U.S. Application Data

[62] Division of Ser. No. 651,107, Jan. 21, 1976, abandoned.

[30] Foreign Application Priority Data

Jan. 27, 1975 [CH] Switzerland ............................ 950/75

[51] Int. Cl.² .................. C07C 103/28; C07C 103/76
[52] U.S. Cl. .............................. 260/558 A; 260/288 R; 260/294.9; 260/295 AM; 260/465 E; 260/558 P; 260/559 D; 260/570 D; 560/36
[58] Field of Search ............ 260/558 A, 558 P, 559 D

[56] References Cited

U.S. PATENT DOCUMENTS 3,647,431  3/1972  Rossi ........................ 260/558 A UX

OTHER PUBLICATIONS

Fosse et al., CA, vol. 2, pp. 823–824, (1968).
Beilstein "Handbuch der Organischen Chemie", vol. 14, p. 176, (1931).
Sashihara et al., CA 83:69111t, (1975).
Garner et al., CA 84: 24454m, (1976).

Primary Examiner—Winston A. Douglas
Assistant Examiner—Thomas A. Waltz
Attorney, Agent, or Firm—Edward McC. Roberts; Prabodh I. Almaula

[57] ABSTRACT

Bis-aminoarylethane compounds of the general formula

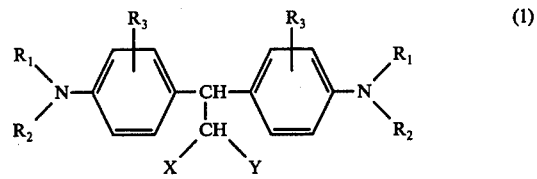

wherein
$R_1$ and $R_2$, which can be the same or different, represent hydrogen, alkyl of at most 12 carbon atoms which is unsubstituted or substituted by cyano or halogen, alkoxyalkyl of 2 to 8 carbon atoms, benzyl or phenyl,
$R_3$ represents hydrogen, halogen, nitro, alkyl of 1 to 4 carbon atoms or alkoxy of 1 to 4 carbon atoms,
X represents an electrophilic group and
Y represents an inert organic group or an electrophilic group, or
X and Y, together with the linkage carbon atom to which they are attached, represent a carbocyclic or 5- or 6-membered heterocyclic ring which contains a keto group adjacent to the linkage carbon atom, with the 5-membered heterocyclic ring containing no nitrogen ring members adjacent to each other.

These compounds are particularly useful as color formers which give intense violet to green colors of excellent light fastness when they are brought into contact with an electron-accepting co-reactant.

5 Claims, No Drawings

BIS-AMINOARYLETHANE AMIDE COMPOUNDS

This is a division of application Ser. No. 651,107 filed on Jan. 21, 1976, now abandoned.

The present invention provides new bis-aminoarylethane compounds, a process for their manufacture and a method of using them in pressure-sensitive recording materials.

The new bis-aminoarylethane compounds have the general formula

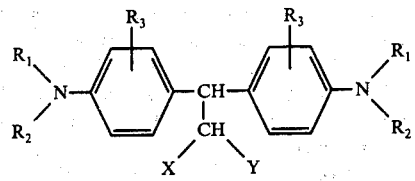

wherein $R_1$ and $R_2$, which can be the same or different, represent hydrogen, alkyl of at most 12 carbon atoms which is unsubstituted or substituted by cyano or halogen, alkoxyalkyl of 2 to 8 carbon atoms, benzyl or phenyl, $R_3$ represents hydrogen, halogen, nitro, alkyl of 1 to 4 carbon atoms or alkoxy of 1 to 4 carbon atoms, X represents an electrophilic group and Y represents an inert organic group or an electrophilic group, or X and Y, together with the linkage carbon atom to which they are attached, represent a carbocyclic or 5- or 6-membered heterocyclic ring which contains a keto group adjacent to the linkage carbon atoms, with the 5-membered heterocyclic ring containing no nitrogen ring members adjacent to each other.

Alkyl groups represented by the substituents $R_1$ and $R_2$ can be branched preferably or straight-chain. Examples of such alkyl radicals are methyl, ethyl, n-propyl, isopropyl, n-butyl, sec. butyl, n-hexyl, n-octyl or n-dodecyl.

Substituted alkyl groups $R_1$ and $R_2$ are primarily haloalkyl and cyanoalkyl groups, each of 2 to 4 carbon atoms, for example β-chloroethyl and β-cyanoethyl groups.

Alkoxyalkyl groups represented by $R_1$ and $R_2$ can contain 1 to 4 carbon atoms in each of the alkyl moieties. Preferred alkoxyalkyl groups are β-methoxyethyl and β-ethoxyethyl groups.

As alkyl, $R_3$ preferably represents methyl, and as alkoxy, represents preferably methoxy and ethoxy.

The grouping

is the radical of a compound containing an active methylene group, which is attached through this methylene group to the bis-arylmethane radical. The electrophilic groups represented by X and Y can be the same or different. Possible electrophilic groups are, for example, nitro, cyano, or acyl groups of 2 to 12 carbon atoms, carboxy ester groups, such as carbalkoxy of 2 to 5 carbon atoms or carbophenoxy which is unsubstituted or ring-substituted, the carboxy amide or sulphonamide group, N-monosubstituted or N,N-disubstituted carbamoyl or sulphamoyl groups with an unsubstituted or substituted phenyl, benzyl and/or alkyl group of 1 to 4 carbon atoms, it being possible for the N,N-substituents of this amide group, together with the nitrogen atom to which they are attached, to form a 5- or 6-membered heterocyclic ring, and also negatively substituted atomatic radicals, for example nitrophenyl, in particular o- and/or p-nitrophenyl, or aromatic heterocyclic rings containing tertiary nitrogen.

As an inert organic group, i.e. a group that is nonreactive and non-activating under the reaction conditions, Y can represents, for example, an alkyl or alkoxy group, each of 1 to 4 carbon atoms, or a phenyl radical which is unsubstituted or substituted by alkyl or alkoxy, each of 1 to 4 carbon atoms. By way of example mention may be made of radicals which are derived from malonic dinitrile, benzylcyanide, cyanoacetic ester and aryl amides and malonic diester and diaryl amides. To be particularly mentioned are the

groupings which derive from methylene compounds with a reactive ketomethylene group. Possible groups in this connection are both those that contain the group in open chain and those in which X and Y, together with the carbon atom to which they are attached, form a carbocyclic or a 5- or 6-membered heterocyclic ring to which a further ring, preferably a benzene ring, can be fused, in which case the 5-membered heterocyclic ring, if present, will contain only one nitrogen atom or nonadjacent nitrogen atoms as ring members.

Examples of open-chain ketomethylene compounds are: aliphatic 1,3-diketones, for example acetylacetone, malonic acid alkyl ($C_1$–$C_4$) and phenyl esters and amides, acylacetic acid alkyl ($C_1$–$C_4$) and phenyl esters and amides whose benzene nuclei are unsubstituted or substituted by methyl, methoxy, ethoxy, cyano, halogen or nitro, for example acetoacetic anilide, acetoacetic chloroanilides, acetoacetic toluidides, acetoacetic xylidides, acetoacetic anisidides, acetoacetic phenitides or benzoylacetic anilide.

Examples of suitable carbocyclic ketomethylene compounds are 1,3-indandione and 5,5-dimethyl-1,3-dioxocyclohexane. Nitrogen-containing 5-membered heterocyclic compounds as defined herein which contain a ketomethylene group are, for example, 2,4-dioxopyrrolidines, hydantoins or the oxindole derivatives. Further heterocyclic components corresponding to the

grouping and containing a ketomethylene group are thiazolones, 2,4-dioxo-tetrahydrofurans, pyronones, hydroxypyridones, 4-hydroxy-2-quinolones, dihydrouracils, 4,6-dioxopyrimidines and barbituric acids. These mononuclear or polynuclear heterocyclic compounds can contain the substituents cited hereinbefore, in particular halogen, cyano, nitro, alkyl of 1 to 4 carbon atoms, alkoxy of 1 to 4 carbon atoms, acyl of 1 to 8 carbon atoms, or phenyl.

In the foregoing definition of the substituents, acyl is to be understood as meaning preferably benzoyl and, in particular, alkanoyl of 2 to 4 carbon atoms, for example acetyl or propionyl. Halogen is, for example, fluorine, bromine or preferably chlorine.

An important group of compounds of formula (1) is that of the general formula

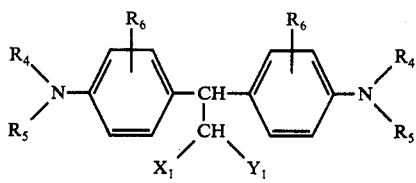
(2)

wherein each of $R_4$ and $R_5$ independently represents hydrogen, alkyl of 1 to 4 carbon atoms or benzyl, $R_6$ represents hydrogen, methyl, methoxy or chlorine, each of $X_1$ and $Y_1$ independently represents cyano, acyl of 2 to 8 carbon atoms, carbalkoxy of 2 to 5 carbon atoms, carbophenoxy or carboxy anilide groups whose benzene nuclei are unsubstituted or substituted by cyano, halogen, nitro, alkyl of 1 to 4 carbon atoms or alkoxy of 1 to 4 carbon atoms, and $Y_1$ can also be alkyl of 1 to 4 carbon atoms or phenyl, or $X_1$ and $Y_1$, together with the linkage carbon atom to which they are attached, form a carbocyclic or 5- or 6-membered heterocyclic ring which contains a keto group adjacent to the linkage carbon atom, and the 5-membered heterocyclic ring can contain at most one nitrogen ring member.

Particularly useful bis-aminoarylethane compounds of formulae (1) and (2) above are those referred to in (A) and (B) hereinafter.

A. Compounds of the general formula

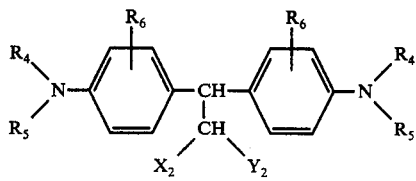
(3)

wherein $R_4$, $R_5$ and $R_6$ are as defined in formula (2), and each of $X_2$ and $Y_2$ independently represents cyano, acyl of 2 to 8 carbon atoms, preferably acetyl or benzoyl, or represents the group of formula

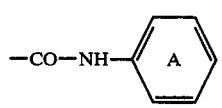
(3.1)

wherein the benzene ring A can be substituted by methyl, methoxy, halogen or nitro.

In these compounds of the general formula (3), $X_2$ preferably represents cyano, acetyl or benzoyl and $Y_2$ preferably represents cyano, acetyl or the group of formula (3.1).

B. Compounds of the general formula

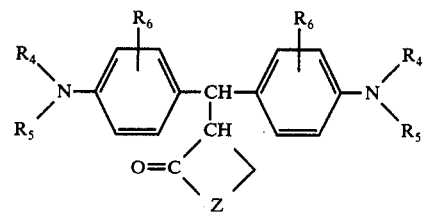
(4)

wherein $R_4$, $R_5$ and $R_6$ are as defined in formula (2) and Z represents those members which are necessary to complete a carbocyclic or a 6-membered heterocyclic ring system. In this respect, Z can also complete a radical which is derived from polynuclear, condensed heterocyclic compounds which preferably contain a fused benzene ring. Examples of such heterocyclic compounds are 5,5-di($C_1$-$C_4$)alkyl-1,3-dioxo-cyclohexane, 1-($C_1$-$C_4$)alkyl-4-hydroxy-2-quinolone, 6-hydroxy-3-cyano- or -carbonamido-4($C_1$-$C_4$)alkyl-2-pyridone or 6-hydroxy-3-cyano- or -carbonamido-1,4-di($C_1$-$C_4$)alkyl-2-pyridone.

Preferred compounds of formula (4) are those in which both $R_4$ and $R_5$ represent methyl or ethyl, $R_6$ represents hydrogen and Z represents those ring members which complete a 5,5-dimethyl-1,3-dioxo-cyclohexyl-(2) or 1-methyl-4-hydroxy-2-quinolyl-(3) radical.

The bis-aminoarylethane compounds of formula (1) or of the subgroup formulae are obtained by known processes. An advantageous process comprises reacting a carbinol or carbinol ether compound of formula

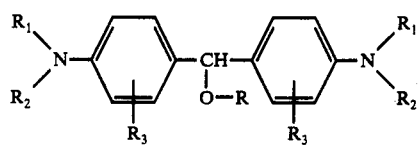
(5)

wherein R represents hydrogen or alkyl of 1 to 4 carbon atoms, for example methyl, and $R_1$, $R_2$ and $R_3$ are as defined hereinbefore, with a methylene compound of the general formula

(6)

wherein X and Y are as defined hereinbefore.

The reaction takes place advantageously in the presence of an alcohol, preferably methanol, and at reflux temperature.

The starting materials of formula (5), wherein R represents hydrogen, are normally obtained by oxidising a bis-aminoarylethane compound of formula

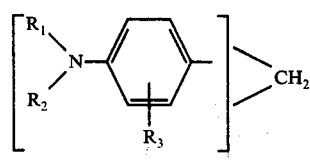
(7)

wherein the conventional oxidants, for example chromates, bichromates, chlorates, peroxides, manganese dioxide, iron(III) salts or permanganates may be used. If desired, the resultant carbinol compounds can be etherified with an alkanol.

The colour formers of formulae (1) to (4) are normally colourless or at most faintly coloured. When they are brought into contact with an acid developer, i.e. an electron acceptor, they produce violet to green colours of excellent light fastness. They are therefore also very useful when mixed with other known colour formers, for example crystal violet lactone, 3,3-(bis-aminophenyl)-phthalide, 3-(aminophenyl-3-indolyl)-phthalide, or benzoyl leucomethylene blue, in order to produce blue, navy blue, grey or black colours.

The colour former mixtures of the compounds of formulae (1) to (4) are suitable above all for use in a pressure-sensitive or heat-sensitive recording material. A pressure-sensitive recording material comprises for example at least a pair of sheets which contain at least one colour former of formulae (1) to (4), dissolved in an organic solvent, and an electron acceptor substance as developer.

Typical examples of such electron acceptors are attapulgite clay, silton clay, silica, bentonite, halloysite, aluminium oxide, aluminium sulphate, aluminium phosphate, zinc chloride, kaolin or any acid clay, or an acid polymeric material, for example a phenolic polymer, an alkylphenolacetylene resin, a maleic acid/rosin resin or a partially or completely hydrolysed polymer of maleic acid and styrene, ethylene, vinyl methyl ether or carboxypolymethylene. Preferred developers are attapulgite clay, silton clay or phenolformaldehyde resin. These electron acceptors are preferably applied in the form of a layer to the face of the receiver sheet.

The colour former effects a coloured marking imprint within, for example, 1 to 4 minutes, at those points at which it comes into contact with the electron acceptor substance.

These colour formers which are present in the pressure-sensitive recording material are normally separated from the electron acceptor substance in order to prevent them from becoming active too soon. This can be accomplished as a rule by incorporating the colour formers in foam-like, sponge-like or honeycomb-like structures. Preferably, however, the colour formers are enclosed in microcapsules which can be ruptured by pressure.

When the capsules are ruptured by pressure, for example with a pencil, and the colour former solution is thus transferred to an adjacent sheet which is coated with an electron acceptor, a coloured image is produced.

The colour formers of formulae (1) to (4) surprisingly are characterised by a high rate of colour development with acid developers in a thermoreactive recording material and at the same time by excellent light fastness. This recording material comprises at least a carrier, a colour former, and electron acceptor substance and optionally a binder. Thermoreactive recording systems comprise heat-sensitive recording and copying materials and papers. These systems are used, for example, for recording information, e.g. in electronic computers, teleprinters or telewriters, and in measuring instruments. The image (mark) formation can also be effected manually with a heated pen. Laser beams can also be used to produce heat-induced marks. The thermoreactive recording material can be so composed that the colour former is dispersed or dissolved in one binder layer and the developer is dissolved or dispersed in the binder in a second layer. A second possibility consists in dispersing both the colour former and the developer in the binder in one layer. By means of heat the binder is softened at specific areas and the colour former comes into contact with the electron acceptor substance at those points at which heat is applied and the desired colour developes at once.

The developers are the same electron-accepting substances as are used in pressure-sensitive papers. For practical purposes the developer should be solid at room temperature and melt or soften above 50° C. Examples of such products are the clays or phenolic resins already mentioned, or phenolic compounds, for example 4-tert. butylphenol, 4-phenylphenol, 4-hydroxydiphenyl oxide, α-naphthol, β-naphthol, 4-hydroxybenzoic acid methyl ester, 4-hydroxyacetophenone, 2,2'-dihydroxydiphenyl, 4,4-isopropylidene-diphenol, 4,4'-isopropylidene-bis-(2-methylphenol), 4,4'-bis-(hydroxyphenyl)valeric acid, hydroquinone, pyrogallol, phloroglucinol, p-, m- and o-hydroxybenzoic acid, gallic acid, 1-hydroxy-2-naphthoic acid, as well as boric acid and aliphatic dicarboxylic acids, e.g. tartaric acid, oxalic acid, maleic acid, citric acid, citraconic acid or succinic acid. Preferably, mixtures of two or more of these substances are also used as developer.

Fusible, film-forming binders are preferably used for the manufacture of the thermoreactive recording material. These binders are normally water-soluble, whereas the colour formers and the developer are insoluble in water. The binder should be able to disperse and fix the colour former and the developer at room temperature. By applying heat the binder softens or melts, so that the colour former comes in contact with the developer and a colour is able to form. Examples of binders which are soluble or at least swellable in water are hydrophilic polymers, for example polyvinyl alcohol, polyacrylic acid, hydroxyethyl cellulose, methyl cellulose, carboxymethyl cellulose, polyacrylic amide, polyvinyl pyrrolidone, gelatin and starch.

If the colour former and the developer are in two separate layers, it is possible to use water-insoluble binders, i.e. binders which are soluble in non-polar or only weakly polar solvents, for example natural rubber, synthetic rubber, chlorinated rubber, alkyd resins, polystyrene, styrene/butadiene copolymers, polymethylmethacrylates, ethyl cellulose, nitrocellulose and polyvinyl carbazole.

The following Examples will serve to illustrate the invention. Unless otherwise indicated, the parts are by weight.

EXAMPLE 1

2.7 g of bis-(4-dimethylaminophenyl)-carbinol and 1.4 g of 5,5-dimethyl-1,3-dioxo cyclohexane are stirred in 50 ml of methanol for 5 hours at reflux temperature. After the reaction mixture has been cooled to 20° C, the precipitated reaction product is filtered off, washed with 30 ml of methanol and dried at 60° C.

Yield: 3.6 g of a colour former of formula

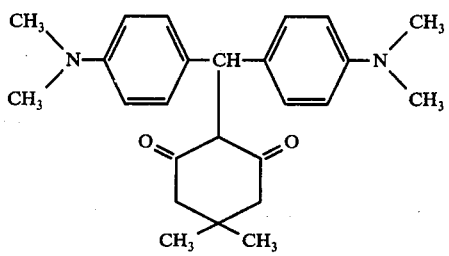

which melts at 170°-174° C.

EXAMPLE 2

The procedure of Example 1 is repeated using equimolar amounts of 1-methyl-4-hydroxy-2-quinolone, acetylacetone, acetoacetic anilide or malonic dinitrile instead of 5,5-dimethyl-1,3-dioxo-cyclohexane, to yield the colour formers of formulae (12) to (15) listed in the following table. The last column of the table indicated the shades, with absorption maxima, which the colour formers develop when brought into contact with silton clay.

Table

| formula | R | R | $Z_1$ | melting point °C | Silton clay colour | $\lambda_1$ | $\lambda_2$ |
|---|---|---|---|---|---|---|---|
| 11 | $CH_3$ | $CH_3$ | (dimethyl-dioxo-cyclohexane) | 170–174 | blue | 616 | 575 |
| 12 | $CH_3$ | $CH_3$ | (1-methyl-4-hydroxy-2-quinolone) | 198–200 | blue | 616 | 573 |
| 13 | $CH_3$ | $CH_3$ | $-CH(COCH_3)_2$ | 142–144 | blue | 616 | 573 |
| 14 | $CH_3$ | $CH_3$ | $-CH(CO-CH_3)-CONH-C_6H_5$ | 201–202 | blue | 616 | 578 |
| 15 | $CH_3$ | $CH_3$ | $-CH(CN)_2$ | 167–169 | blue | 616 | 576 |

We claim:

1. A bis-aminoarylethane compound of the formula

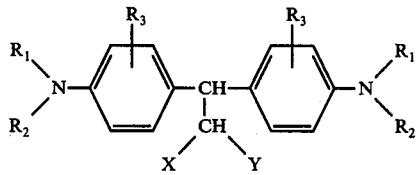

(1)

wherein $R_1$ and $R_2$, which can be the same or different, represent hydrogen, alkyl of at most 12 carbon atoms which is unsubstituted or substituted by halogen, alkoxyalkyl of 2 to 8 carbon atoms, benzyl or phenyl, $R_3$ represents hydrogen, halogen, nitro, alkyl of 1 to 4 carbon atoms or alkoxy of 1 to 4 carbon atoms, each of X and Y independently represents carboxy anilide groups whose benzene nuclei are unsubstituted or substituted by halogen, nitro, alkyl of 1 to 4 carbon atoms or alkoxy of 1 to 4 carbon atoms, and Y is also alkyl of 1 to 4 carbon atoms, acyl of 2 to 8 carbon atoms or phenyl.

2. The bis-aminoarylethane compound of claim 1, wherein each of $R_1$ and $R_2$ independently represents hydrogen, alkyl of 1 to 4 carbons atoms or benzyl and $R_3$ represents hydrogen, methyl, methoxy or chlorine.

3. The bis-aminoarylethane compound of claim 1, wherein each of X and Y independently represents the group

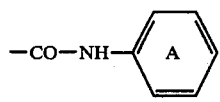

wherein the benzene ring A is unsubstituted or substituted by methyl, methoxy, halogen or nitro and Y is also acyl of 2 to 8 carbon atoms.

4. The compound of claim 3 wherein Y represents acetyl or benzoyl and X represents the group

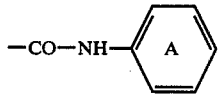

5. The compound of claim 4 wherein $R_1$ and $R_2$ are methyl, $R_3$ is hydrogen, Y is acetyl and X is

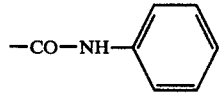

* * * * *